US007637898B2

(12) United States Patent  
Kuen et al.

(10) Patent No.: US 7,637,898 B2
(45) Date of Patent: Dec. 29, 2009

(54) DISPOSABLE ABSORBENT PANT HAVING REFASTENABLE SEAMS

(75) Inventors: David Arthur Kuen, Neenah, WI (US); Robert Lee Popp, Hortonville, WI (US); Heather Schenck Mortell, Neenah, WI (US)

(73) Assignee: Kimberly-Clark Wordwide, Inc., Neenah, WI (US)

( * ) Notice: Subject to any disclaimer, the term of this patent is extended or adjusted under 35 U.S.C. 154(b) by 1333 days.

(21) Appl. No.: 10/222,216

(22) Filed: Aug. 16, 2002

(65) Prior Publication Data

US 2004/0034327 A1 Feb. 19, 2004

(51) Int. Cl.
*A61F 13/15* (2006.01)
*A61F 13/20* (2006.01)
(52) U.S. Cl. ............... 604/391; 604/386; 604/389; 604/394
(58) Field of Classification Search ............ 604/385.11, 604/389, 390
See application file for complete search history.

(56) References Cited

U.S. PATENT DOCUMENTS

| 2,957,512 | A | 10/1960 | Wade et al. .............. 154/33.05 |
| 3,319,307 | A | 5/1967 | Marforio .................... 24/204 |
| 3,577,607 | A | 5/1971 | Ikoma et al. ................ 24/204 |
| 3,694,867 | A | 10/1972 | Stumpf ....................... 24/204 |
| 3,943,981 | A | 3/1976 | De Brabander ............ 139/391 |
| 4,205,679 | A | 6/1980 | Repke et al. ............... 128/287 |
| 4,610,680 | A | 9/1986 | LaFleur ................ 604/385 A |
| 4,615,695 | A | 10/1986 | Cooper .................. 604/385 A |
| 4,699,622 | A | 10/1987 | Toussant et al. ............ 604/389 |
| 4,705,710 | A | 11/1987 | Matsuda ...................... 428/92 |
| 4,714,096 | A | 12/1987 | Guay ........................ 139/391 |
| 4,761,318 | A | 8/1988 | Ott et al. ...................... 428/85 |
| 4,940,464 | A | 7/1990 | Van Gompel et al. ....... 604/396 |
| 4,963,140 | A | 10/1990 | Robertson et al. |
| 5,032,122 | A | 7/1991 | Noel et al. .................. 604/391 |
| 5,087,253 | A | 2/1992 | Cooper ................... 604/385.1 |
| 5,176,671 | A | 1/1993 | Roessler et al. |
| 5,256,231 | A | 10/1993 | Gorman et al. ............. 156/178 |
| 5,326,612 | A | 7/1994 | Goulait ....................... 428/100 |

(Continued)

FOREIGN PATENT DOCUMENTS

EP 0 812 584 A2 12/1997

(Continued)

OTHER PUBLICATIONS

Zheng et al, Evaluating Shear Rigidity of Woven Fabrics, Textile Research Journal, 76:2, pp. 145-151.*

*Primary Examiner*—Melanie J Hand
(74) *Attorney, Agent, or Firm*—Armstrong Teasdale, LLP

(57) ABSTRACT

A disposable absorbent pant having refastenable seams that minimize the product's potential for tearing when forces are applied to separate the refastenable seams. More particularly, the refastenable seams have a shear separation strength that is less than a tensile or tear strength of the outer cover and/or side panels. Also, the bonding strength between a fastening component and the portion of the chassis to which the fastening component is bonded may be greater than the shear separation strength of the refastenable seams. Additionally, the shear separation strength of the refastenable seams may be greater than the peel separation strength of the refastenable seams to enable easy unfastening of the garment through the application of peel forces.

26 Claims, 4 Drawing Sheets

U.S. PATENT DOCUMENTS

| | | | |
|---|---|---|---|
| 5,370,634 A | 12/1994 | Ando et al. | 604/385.1 |
| 5,407,439 A | 4/1995 | Goulait | 604/391 |
| 5,595,567 A | 1/1997 | King et al. | 604/391 |
| 5,615,460 A | 4/1997 | Weirich et al. | 24/446 |
| 5,616,394 A | 4/1997 | Gorman et al. | 428/99 |
| 5,624,427 A | 4/1997 | Bergman et al. | 604/391 |
| 5,647,864 A | 7/1997 | Allen et al. | 604/391 |
| 5,649,921 A * | 7/1997 | Arakawa et al. | 604/390 |
| 5,669,900 A | 9/1997 | Bullwinkel et al. | 604/391 |
| 5,830,206 A | 11/1998 | Larsson | 604/390 |
| 5,830,298 A | 11/1998 | Jackson | 156/66 |
| 5,855,574 A | 1/1999 | Kling et al. | 604/392 |
| 5,888,607 A | 3/1999 | Seth et al. | 428/92 |
| 5,891,547 A | 4/1999 | Lawless | 428/92 |
| 5,897,545 A | 4/1999 | Kline et al. | 604/386 |
| 5,897,547 A | 4/1999 | Schmitz | 604/391 |
| 5,910,224 A | 6/1999 | Morman | |
| 5,997,981 A | 12/1999 | McCormack et al. | 428/99 |
| 6,027,485 A | 2/2000 | Matsushita et al. | 604/391 |
| 6,146,738 A | 11/2000 | Tsuji et al. | 428/99 |
| 6,287,287 B1 | 9/2001 | Elsberg | 604/385.03 |
| 6,328,725 B2 | 12/2001 | Fernfors | 604/391 |
| 6,329,016 B1 | 12/2001 | Shepard et al. | 427/173 |
| 6,332,250 B1 | 12/2001 | Igaue et al. | 24/450 |
| 6,461,344 B1 | 10/2002 | Widlund et al. | 604/390 |
| 6,716,205 B2 * | 4/2004 | Popp et al. | 604/385.24 |
| 2002/0003022 A1 | 1/2002 | Csida et al. | |

FOREIGN PATENT DOCUMENTS

| | | |
|---|---|---|
| EP | 0 989 222 A1 | 3/2000 |
| EP | 989222 A1 * | 3/2000 |
| EP | 0989222 A1 * | 3/2000 |
| FR | 1375254 | 9/1964 |
| GB | 2 296 422 A | 7/1996 |
| GB | 2296422 A * | 7/1996 |
| WO | WO 00/35398 | 6/2000 |
| WO | WO 00/37009 | 6/2000 |
| WO | WO 00/37016 | 6/2000 |
| WO | WO 01/43684 A1 | 6/2001 |
| WO | WO 02/41816 A2 | 5/2002 |
| WO | WO 02/053078 A1 | 7/2002 |

\* cited by examiner

DISPOSABLE ABSORBENT PANT HAVING REFASTENABLE SEAMS

BACKGROUND OF THE INVENTION

This invention is directed to a disposable absorbent pant having refastenable seams designed to minimize the likelihood of product tearing when forces are applied to separate the refastenable seams.

Disposable absorbent pants are used as a child's segue from diapers to underwear. Unlike diapers, which have high-cut leg openings with tabs or ears that fasten to the front of the waist area, disposable absorbent pants are designed to more closely resemble underwear with side seams on opposite sides of the garment that extend from a waist opening to well-defined leg openings. Consequently, diapers can be fastened to a wearer while the wearer is lying on his or her back with the fastening occurring on the wearer's front. In contrast, disposable absorbent pants typically have side seams along the wearer's side, which can make it difficult for a caregiver to fasten, unfasten, or even tear apart the side seams of the disposable absorbent pant, particularly on an active toddler. Another difference between diapers and disposable absorbent pants is that disposable absorbent pants can be slid on and off a wearer just like underwear.

One particularly beneficial improvement to disposable absorbent pants has been the creation of refastenable side seams in lieu of permanently bonded side seams. With the refastenable side seams, the disposable absorbent pant can still be pulled on and off like underwear, but also provides the option of being able to unfasten either side to determine whether a need exists to change the disposable absorbent pant. If the disposable absorbent pant is unfastened and it is determined that there is no need to change the disposable absorbent pant, the pant can be easily refastened. Additionally, if it is determined that the disposable absorbent pant is soiled and should therefore be changed, the caregiver can unfasten the garment along the refastenable seams and remove the garment without the necessity of removing the wearer's other garments. By removing the garment this way, the contents of the garment can also be more easily contained compared to having to slide the garment off the wearer in the manner of removing conventional underwear.

Many caregivers remove the disposable absorbent pants from a wearer by applying force to the side seams in opposing directions, whether the side seams are permanently bonded or refastenable. Generally, disposable absorbent pants having permanently bonded side seams tear adjacent the side seams or in another weakened area when such force is applied in the side seam region. It has also been observed that disposable absorbent pants having refastenable side seams sometimes tear at the side panels or the outer cover, or fastening components may become detached from the region of the garment to which they are bonded, or layers of the garment may start to delaminate, when such force is applied to the refastenable side seam region of the garment. Thus, if the refastenable side seams are too strong, or at least stronger than other materials in the garment, rather than becoming unfastened at the seam the other components of the garment may become irreparably damaged when any sufficiently large force is applied to the garment, either during normal wear and tear or when a caregiver is checking the status of the garment, thereby requiring replacement of the garment even if the garment is not soiled.

Furthermore, certain types of fasteners tend to increase in shear strength during wear and tear. For example, hook and loop fasteners tend to become more securely engaged during certain types of wear and tear because more and more hooks come into contact with more and more loops as the hook and loop fasteners are contorted during certain actions. Thus, by the time a caregiver checks the garment for any soiling, the refastenable seam may be more difficult to unfasten than it was when it was first fastened.

As another consideration, even if the peel strength of the refastenable seam is lower than the shear strength of the refastenable seam, the garment may still be prone to irreparable damage when high shear stresses are applied because greater force is required to cause shearing of a refastenable seam than to cause peeling of a refastenable seam, and the greater shear force that is needed to separate the seam has different effects on the garment than the relatively mild stresses needed to peel the seam. On the other hand, if the refastenable side seams have too little shear strength, fastener pop-opens are likely to occur as a result of even minimal shear stresses.

There is a need or desire for a refastenable disposable absorbent pant that minimizes the likelihood of irreparable damage resulting from the application of shear stress to the refastenable side seams.

SUMMARY OF THE INVENTION

In response to the discussed difficulties and problems encountered in the prior art, a refastenable disposable absorbent pant that can withstand shear stress at the side seams without undergoing, or at least minimizing, irreparable damage has been discovered.

The disposable absorbent pant includes a chassis with a waist opening and a pair of leg openings defined therein. The chassis includes a front region and a back region, and may include, but does not necessarily include, a pair of front side panels and/or a pair of back side panels attached to front and/or back center panels, respectively. The chassis may also include an outer cover and a body side liner encompassing the front and back regions. A pair of refastenable seams flanks the garment, with each refastenable seam extending from the waist opening to one of the leg openings between the front region and the back region.

The refastenable seams suitably have a shear separation strength that is less than a tearing or tensile strength of the outer cover or other material of the front and back regions. In one embodiment, the ratio of shear separation strength of one of the refastenable seams to tensile strength of the material of the front and back regions is between about 0.01 and about 0.99 per unit of seam length.

In an embodiment in which the disposable absorbent pant includes a pair of front side panels and/or a pair of back side panels permanently bonded to a front and/or back center panel, the shear separation strength of the refastenable seams is suitably less than a bonding strength of the seams connecting the front and back side panels to the front and back center panels. In another embodiment, the ratio of shear separation strength of one of the refastenable seams to bonding strength of one of the chassis seams connecting a front or back side panel to a front or back center panel is between about 0.01 and about 0.99 per unit of seam length.

The refastenable seams may include a fastening component bonded to the outer cover, body side liner, or side panel, and the fastening component may be fastenable with either a mating fastening component bonded to the outer cover, body side liner, or another side panel, or the fastening component may be fastenable with a component of the chassis itself, such as the outer cover, body side liner, or side panel.

The shear separation strength of the refastenable seams is suitably greater than a peel separation strength of the refastenable seams, and a bonding strength between the fastening component and the chassis is suitably greater than the shear separation strength of the refastenable seams. Also, the portion of the chassis to which the fastening component is bonded suitably has a delamination strength greater than the shear separation strength of the refastenable seam that includes the fastening component, such that the chassis material does not delaminate under shear mode stresses that separate the refastenable seam. In yet another embodiment, the ratio of peel separation strength of one of the refastenable seams to shear separation strength of the same refastenable seam is between about 0.01 and about 0.99 per unit of seam length. In still another embodiment, the ratio of shear separation strength of one of the refastenable seams to bonding strength between one of the fastening components within the refastenable seam and the portion of the chassis to which the fastening component is bonded is between about 0.01 and about 0.99 per unit of seam length.

Suitably, the shear separation strength of each of the refastenable seams is between about 0.3 and about 2.7 kilograms (kg), as measured by the tensile test method described in detail below. In one embodiment, the refastenable seams have greater shear separation strength along a waist-end portion and along a leg-end portion of the seam compared to a mid-portion of the seam. Any of the materials in the side seam region, such as the outer cover, body side liner, front region, back region, front side panel, and/or back side panel, may be stretchable.

With the foregoing in mind, it is a feature and advantage of the invention to provide a disposable absorbent pant with refastenable seams that are designed to become unfastened prior to any irreparable damage occurring to the remainder of the garment resulting from the application of shear forces.

BRIEF DESCRIPTION OF THE DRAWINGS

These and other objects and features of this invention will be better understood from the following detailed description taken in conjunction with the drawings, wherein.

DEFINITIONS

Figure 1:
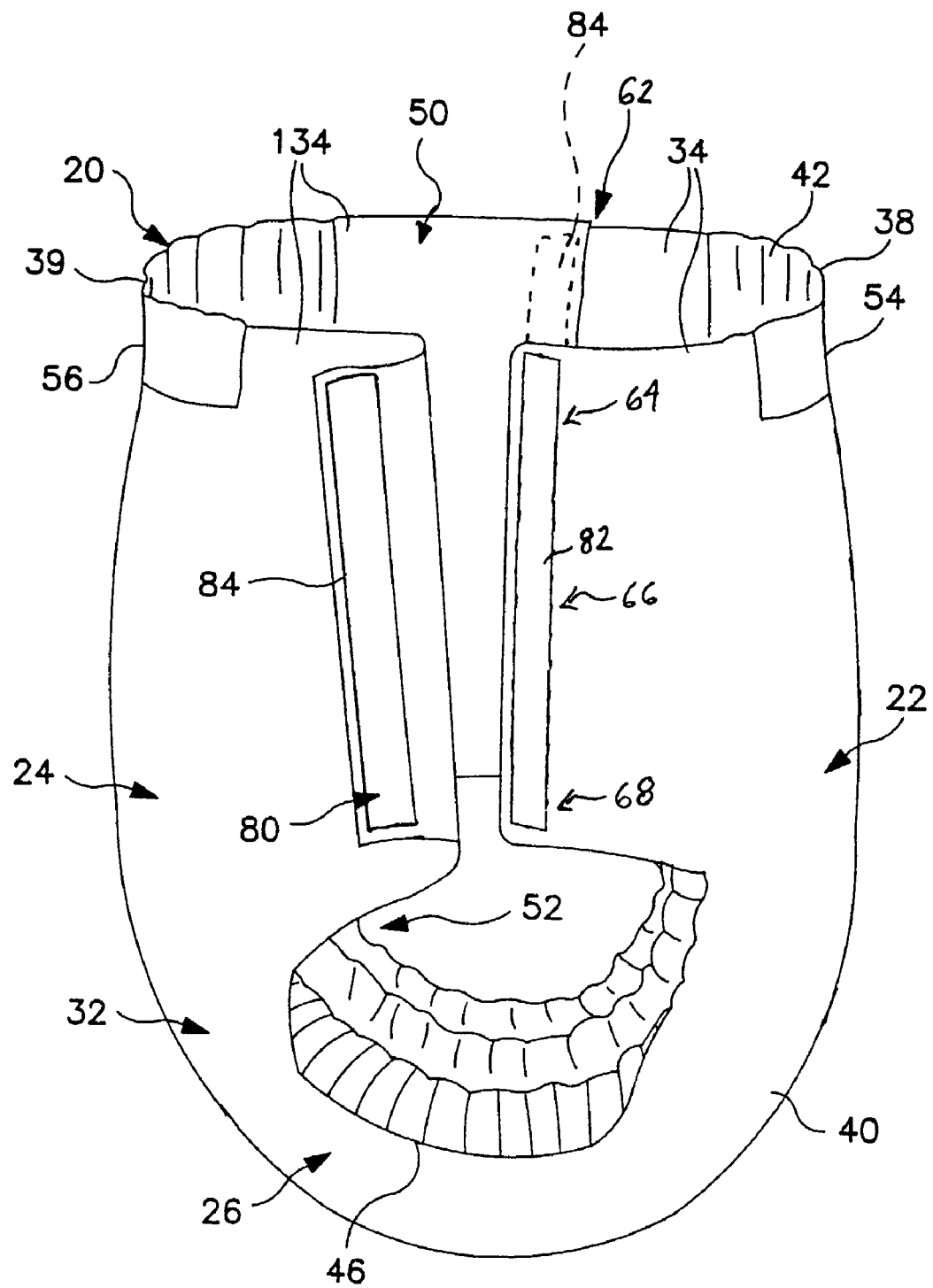
FIG. 1 is a side perspective view of a disposable absorbent pant having refastenable seams.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Bonding strength" refers to the minimum amount of force necessary to separate two bonded elements.

"Delamination strength" refers to the minimum amount of force necessary to separate two laminated layers.

"Disposable absorbent pant" is an all-inclusive term that applies to training pants, diaper pants, disposable absorbent underpants, and other pant-like absorbent garments worn by children subsequent to a diaper-wearing stage.

"Layer" when used in the singular can have the dual meaning of a single element or a plurality of elements.

"Nonwoven" or "nonwoven web" refers to materials and webs or material having a structure of individual fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Peel force" refers to a force that tends to pull two adjoined bodies away from one another in opposite directions generally perpendicular to a plane in which the bodies are joined.

"Peel separation strength" refers to the minimum amount of peel force required to separate two joined elements.

"Refastenable" refers to the property of two elements being capable of releasable attachment, separation, and subsequent releasable attachment without substantial permanent deformation or rupture.

"Releasably attached," "releasably engaged," and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Shear force" refers to forces that tend to produce an opposite but parallel sliding motion between two bodies' planes.

"Shear separation strength" refers to the amount of shear force required to separate two joined elements.

"Stretchable" means that a material can be stretched, without breaking, by 50% to at least 150% of its initial (unstretched) length in at least one direction, suitably to at least 200% of its initial length, desirably to at least 300% of its initial length.

"Superabsorbent" refers to a water-swellable, water-insoluble organic or inorganic material capable, under the most favorable conditions, of absorbing at least about 15 times its weight and, more desirably, at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers.

These terms may be defined with additional language in the remaining portions of the specification.

DESCRIPTION OF PREFERRED EMBODIMENTS

The present invention is directed to a disposable absorbent pant having refastenable side seams for ease of removal and donning of the disposable absorbent pant without complete removal of a wearer's clothing. The refastenable side seams are designed with sufficient shear separation strength to remain fastened during normal wear yet low enough shear separation strength to prevent or minimize irreparable damage to other parts of the disposable absorbent pant during intentional unfastening and/or excessive wear.

Figure 2:
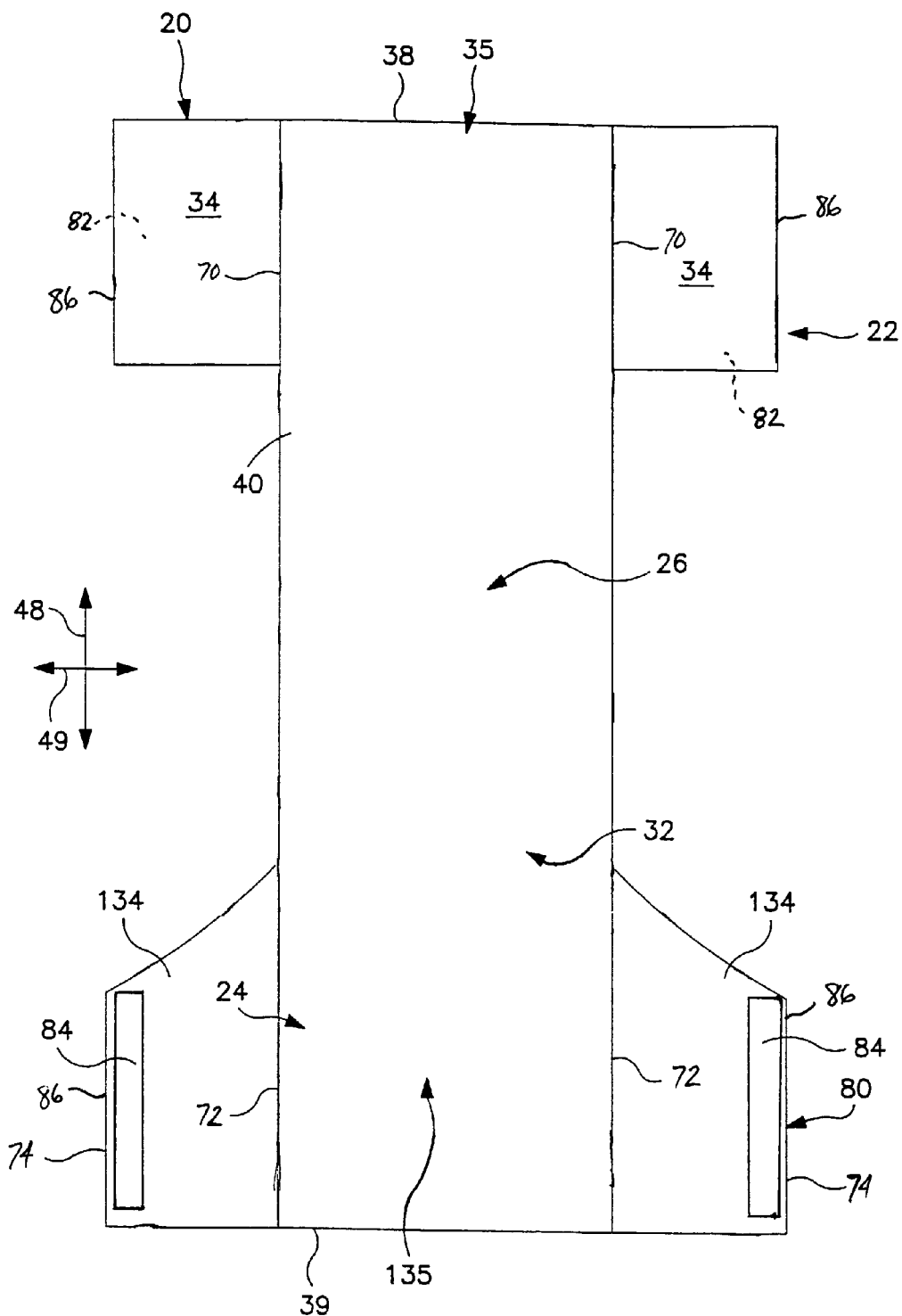
FIG. 2 is a plan view of a disposable absorbent pant in a partially disassembled, stretched flat state, and showing the surface of the article that faces away from the wearer when the article is worn.
Figure 3:
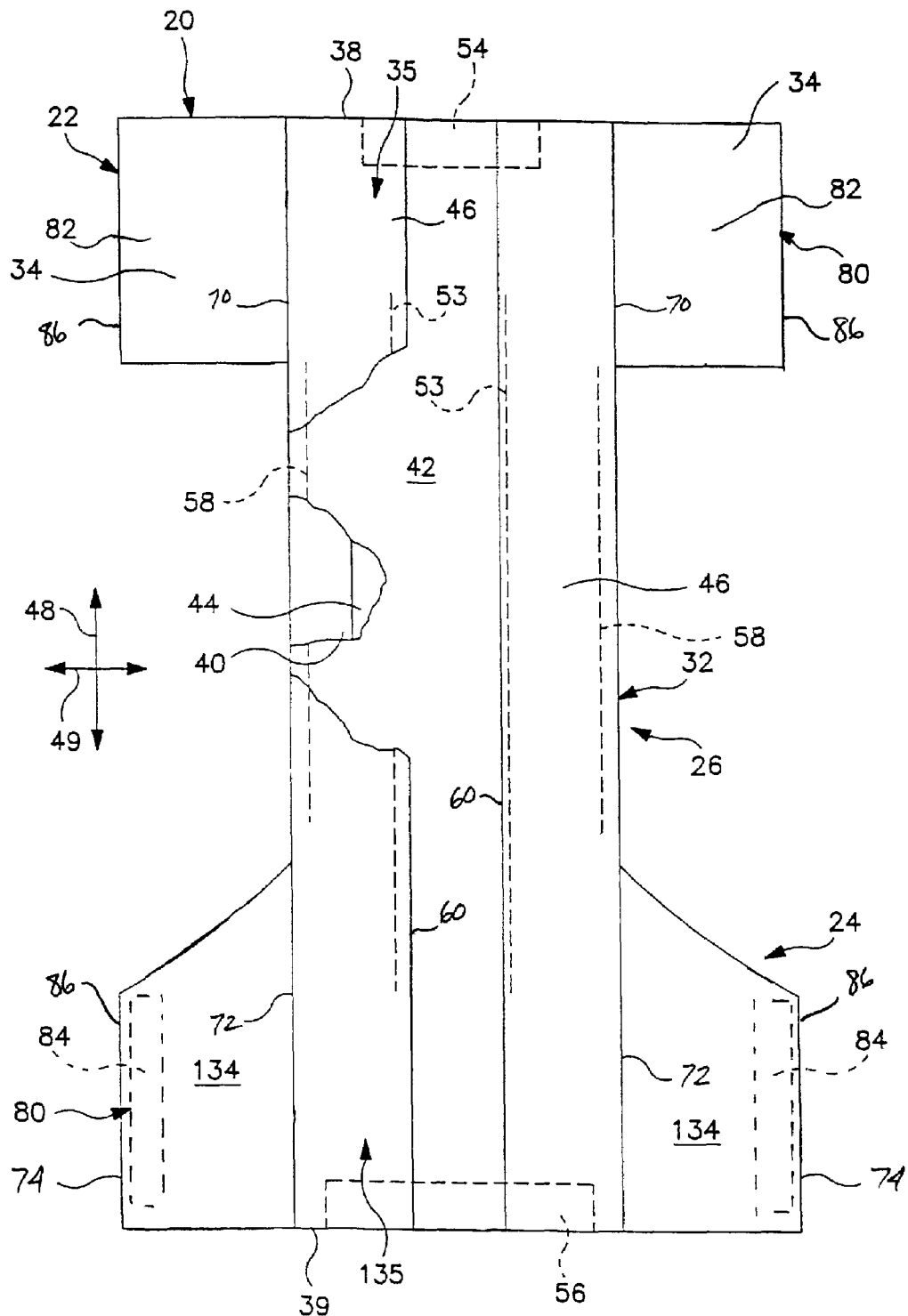
FIG. 3 is a plan view of the disposable absorbent pant of FIG. 2 in a partially disassembled, stretched flat state, and showing the surface of the article that faces the wearer when the article is worn, and with portions cut away to show the underlying features.

Referring to FIG. 1, a disposable absorbent pant 20 is illustrated in a partially fastened condition. The disposable absorbent pant 20 includes a chassis 32 and a fastening system 80. The chassis 32 defines a front region 22, a back region 24, and a crotch region 26 interconnecting the front and back regions. With additional reference to FIGS. 2 and 3, the chassis 32 also includes a pair of transversely opposed front side panels 34 and a pair of transversely opposed back side panels 134. The front side panels 34 may either be separately attached to a front center panel 35 (FIGS. 2 and 3), or may be integrally formed with the front region 22 (FIG. 1). Similarly, the back side panels 134 may either be separately attached to a back center panel 135 (FIGS. 2 and 3), or may be integrally formed with the back region 24. With additional reference to FIGS. 2 and 3, the chassis 32 also defines a pair of longitudinally opposed waist edges, which are designated front waist edge 38 and back waist edge 39. The front region 22 is contiguous with the front waist edge 38, and the back region 24 is contiguous with the back waist edge 39. For reference, arrows 48 and 49 depicting the orientation of the longitudinal axis and the transverse axis, respectively, or the disposable absorbent pant 20 are illustrated in FIGS. 2 and 3.

The chassis 32 includes a body side liner 42 which is configured to contact the wearer, and an outer cover 40 opposite the body side liner which is configured to contact the wearer's clothing. An absorbent assembly 44 (FIG. 3) is positioned or located between the outer cover 40 and the body side liner 42.

With the disposable absorbent pant 20 in the fastened position, as partially illustrated in FIG. 1, the front and back regions 22 and 24 are joined together to define a three-dimensional pant configuration having a waist opening 50 and a pair of leg openings 52. The front region 22 includes the portion of the disposable absorbent pant 20 which, when worn, is positioned on the front of the wearer while the back region 24 includes the portion of the disposable absorbent pant which, when worn, is positioned on the back of the wearer. The crotch region 26 of the disposable absorbent pant 20 includes the portion of the disposable absorbent pant which, when worn, is positioned between the legs of the wearer and covers the lower torso of the wearer.

A pair of refastenable seams 62, each extending from the waist opening 50 to one of the leg openings 52 along opposite sides of the disposable absorbent pant, connects the front region 22 to the back region 24. Garments having refastenable seams are taught, for example, in U.S. Pat. No. 5,176,671 issued Jan. 5, 1993 to Roessler et al. The fastening system 80 may include fastening components 82 that are adapted to refastenably connect to mating fastening components 84. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84. The garment can have front and back regions 22, 24 of different widths, as long as the refastenable seams 62 each begin at the waist opening 50 and end at one of the leg openings 52.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. Alternatively, other types of fastening components, such as tapes, adhesives, cohesives, self-engaging fasteners, or other types of mechanical fasteners, can also be used.

Loop type fasteners typically include a fabric or material having a structure and a plurality of loop members on at least one surface of the structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. In one embodiment, the outer cover material and/or the body side liner material and/or the side panel material may serve as a loop type fastener, thus requiring no separately attached loop type fasteners. Loop materials can also be made up of any fibrous structure capable of entangling or catching hook materials, such as carded, spunbonded, or other nonwoven webs or composites, including elastomeric and nonelastomeric composites.

Hook type fasteners typically include a fabric or material having a plurality of hook members extending upwardly from at least one surface of the backing structure. Suitable single-sided hook materials for the fastening components 82 or the mating fastening components 84 are available from Velcro Industries B.V., Amsterdam, Netherlands or affiliates thereof. In one embodiment, the outer cover material and/or the body side liner material and/or the side panel material may serve as a hook type fastener.

The front side panels 34 may overlap the back side panels 134, or vice-versa, with the fastening component 82 attached to an inner surface of the front side panel 34 and the mating fastening component 84 attached to an outer surface of the back side panel 134, or vice-versa. The fastening component 82 on each front side panel 34 can be bonded to the front side panel adjacent a distal edge 86 of the front side panel, as shown in FIGS. 2 and 3. Similarly, the mating fastening component 84 on each back side panel 36 can be bonded to the back side panel adjacent a distal edge 86 of the back side panel, as shown in FIGS. 2 and 3. In one embodiment (not shown), the fastening components 82 and/or mating fastening components 84 can be bonded to the respective side panel adjacent a distal edge 86 and may extend beyond the distal edge 86.

Once fastened, the refastenable seams 62 can be unfastened with a shear separation strength of between about 0.3 and about 2.7 kilograms (kg), or between about 0.5 and about 1.7 kg, or between about 0.7 and about 1.2 kg, each of these values pertaining to a 1-inch wide sample or a value normalized to a 1-inch wide sample. Shear separation strength of the refastenable seams 62 can be controlled through a variety of factors, including but not limited to, the length-to-width ratio of the fastening components 82 and mating fastening components 84, the choice of fastening components 82, 84 such as hooks having particular binding strengths and loops having particular binding strengths, as well as the shape, orientation, and size of the individual hooks, and/or the number of hooks and/or number of loops. Fastening strength can also be affected by the type of loop material with respect to thread strength which can affect the strength of the material itself and/or denier of the material.

In one embodiment, the refastenable seams 62 may have greater shear separation strength along a waist-end portion 64 and/or along a leg-end portion 68 of each seam compared to a mid-portion 66 of each seam. As used herein, the term "waist-end portion" refers to one-third or less of the longitudinal length of the refastenable seam, as measured starting from the waist opening 50; the term "leg-end portion" refers to one-third or less of the longitudinal length of the refastenable seam, as measured starting from the leg opening 52; and "mid-portion" refers to one-third or more of the longitudinal length of the refastenable seam situated between the waist-end portion 64 and the leg-end portion 68.

In one embodiment, the shear separation strength of the refastenable seams 62 is suitably less than a tensile strength, or tear strength, of the material from which the front and back regions 22, 24 are made. That way, when shear force is applied to the disposable absorbent pant 20, rather than the front or back region tearing, one or both of the refastenable seams 62 will come unfastened. For example, the material from which the outer cover 40 and/or the side panels 34, 134 are made should have a tensile strength greater than the shear separation strength of the refastenable seams 62 to avoid irreparable damage to the outer cover 40 and/or the side panels 34, 134. More particularly, the disposable absorbent pant 20 suitably has a ratio of shear separation strength of the refastenable seams 62 to tensile strength of the front and back regions of between about 0.01 and about 0.99, or between about 0.1 and about 0.9, or between about 0.3 and about 0.8, per unit of seam length. Furthermore, the materials from which the front and back regions 22, 24 are made, namely the materials that make up the outer cover 40 and/or side panels 34, 134, suitably have a delamination or tear strength greater than the shear separation strength of the refastenable seams 62.

In an embodiment in which the front region 22 includes a front center panel 35 with two front side panels 34 bonded thereto along front chassis seams 70 (FIGS. 2 and 3), and/or the back region 24 includes a back center panel 135 with two back side panels 134 bonded thereto along back chassis seams 72 (FIGS. 2 and 3), the front and/or back chassis seams 70, 72 suitably have a greater bonding strength than the shear separation strength of the refastenable seams 62. More particularly, the disposable absorbent pant 20 suitably has a ratio of shear separation strength of the refastenable seams 62 to bonding strength of the front and/or back chassis seams 70, 72 of between about 0.01 and about 0.99, or between about 0.1 and about 0.9, or between about 0.3 and about 0.8, per unit of seam length. Bonding strength of the chassis seams 70, 72 can be controlled through a number of factors, including but not limited to the type of bonding used to bond the side panel to the center panel such as ultrasonic, adhesive, or a combination of ultrasonic and adhesive; the amount of adhesive used; the bond pattern; the amount of overlap between the side and center panels and the amount of overlap bonded; material strengths; and location of the bonded area such as positioning one layer of one panel between two layers of the other panel.

Additionally, the refastenable seams 62 suitably have greater shear separation strength than peel separation strength. Peel separation strength of the seams 62 can be controlled using the same factors used in controlling the shear separation strength of the seams 62. Furthermore, fasteners such as hook and loop fasteners and adhesive fasteners inherently have a greater shear separation strength than peel separation strength by virtue of the fact that peel separation is carried out by separating just a few hook-and-loop couplings at a time, whereas shear separation requires the separation of essentially all hook-and-loop couplings at the same time. By making the seams easier to unfasten using peel force compared to shear force, consumers would be more likely to apply peel forces rather than shear forces when attempting to unfasten the disposable absorbent pant, thus further reducing the likelihood of causing any irreparable damage to the disposable absorbent pant.

In a further embodiment of the invention, bonding strength between the chassis 32 and the fastening components 82 and/or mating fastening components 84 is greater than the shear separation strength of the refastenable seams 62. More particularly, the disposable absorbent pant 20 suitably has a ratio of shear separation strength of the refastenable seams 62 to bonding strength between the chassis 32 and the fastening components 82 and/or mating fastening components 84 of between about 0.01 and about 0.99, or between about 0.1 and about 0.9, or between about 0.3 and about 0.8, per unit of seam length. Bonding strength between the chassis 32 and the fastening components 82, 84 can be controlled using the same factors used in controlling the bonding strength of the chassis seams 70, 72. With these variations in strength, when shear force is applied to the disposable absorbent pant 20, the refastenable seam 62 should come unfastened rather than a fastening component 82 or mating fastening component 84 becoming detached from the chassis 32.

Figure 4:
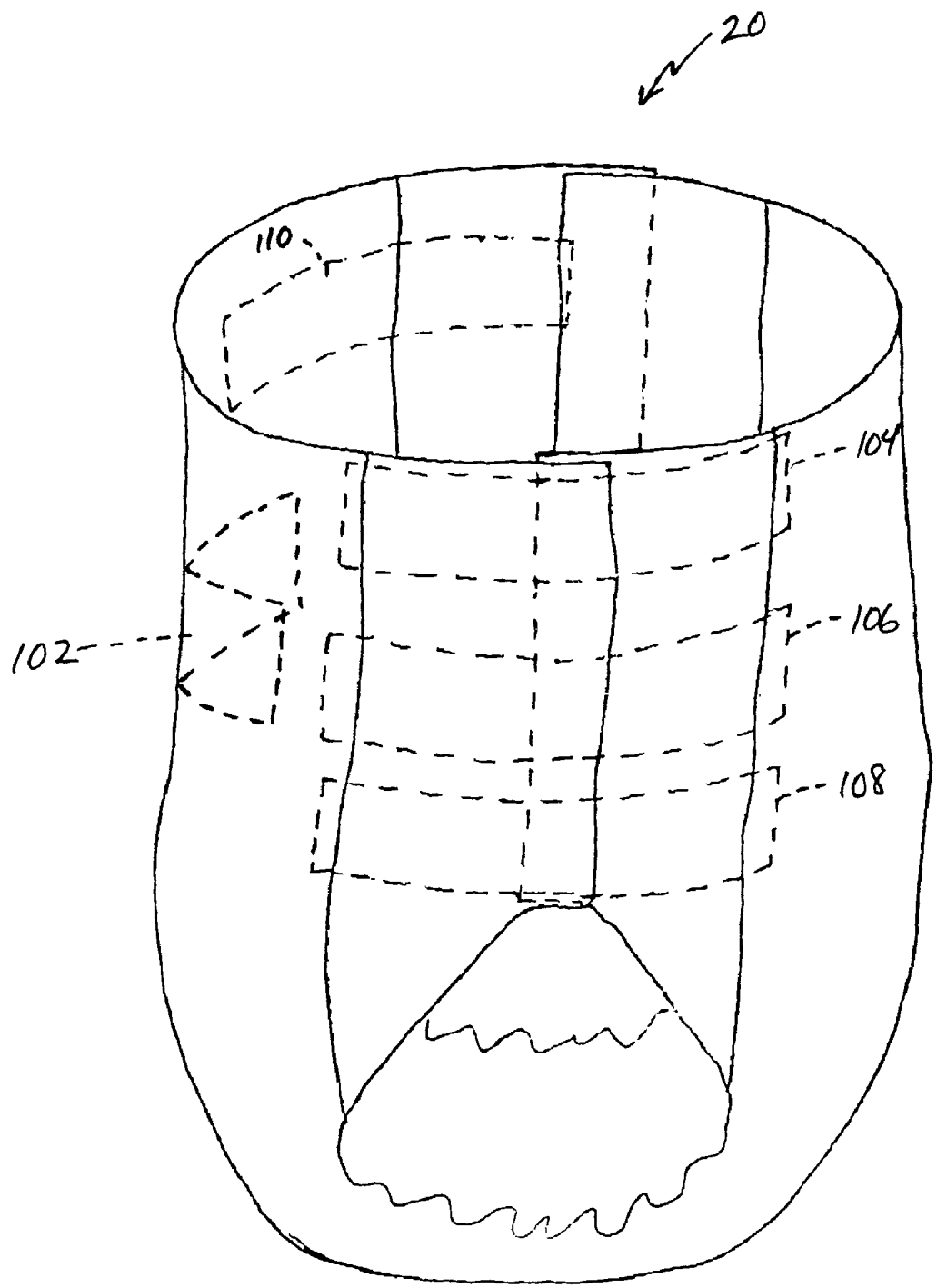
FIG. 4 is a side perspective view of a disposable absorbent pant illustrating orientations of sample material suitable for testing in accordance with the Tensile Test described herein.

The tensile test method, described below, can be used to determine shear separation strength, tensile or tear strength, bonding strength, and even delamination strength. Reported values are derived from testing the fastening system or material in a direction parallel to the transverse axis 49 of the product, when the fastening system or material is installed in a product. FIG. 4 illustrates the orientations of a sample of material 102, fastener regions 104 (waist-end), 106 (mid-portion), 108 (leg-end), or bonded chassis seam region 110 taken from a product. Several variations are possible, depending on the system being tested and on whether the shear strength of the refastenable seam is substantially uniform over its entire length, or whether the seam possesses greater shear strength near leg and waist openings than in the middle region of the seam.

Even if the shear force is caused by motions other than those intended to unfasten the disposable absorbent pant, it is preferable for the refastenable seam 62 to come unfastened as opposed to a fastening component 82, 84 becoming detached from the chassis 32, or a tear forming in the chassis 32, or delamination of the chassis 32, or a tear along the chassis seams 70, 72, all of which are irreparable damage that renders the disposable absorbent pant useless and in need of replacement. In contrast, when a refastenable seam 62 comes unfastened, the seam can easily be refastened without the need for replacing the disposable absorbent pant all together.

The side panels 34, 134 desirably include an elastic material capable of stretching in a direction generally parallel to the transverse axis 49 of the disposable absorbent pant 20. Suitable elastic materials, as well as processes of incorporating side panels into a disposable absorbent pant, are known to those skilled in the art, and are described, for example, in U.S. Pat. No. 4,940,464 issued Jul. 10, 1990 to Van Gompel et al., which is incorporated herein by reference.

One of the key structural differences between disposable absorbent pants and diapers is in the length and location of the side seams. Diapers typically have relatively longitudinally short tabs that fasten to the front of the garment in close proximity to one another. Diaper tabs are easy to see and are generally easy for a caregiver to access, positioned in such a way that a caregiver can open the diaper using one hand on each tab and peeling each tab back. In contrast, disposable absorbent pants generally have seams, refastenable or permanently bonded, that extend from the waist opening to the leg opening on diametrically opposed sides of the wearer such that both seams are not visible at the same time and are therefore more difficult to unfasten, compared to diaper tabs. Consequently, a caregiver often ends up feeling around for the seam or surrounding material, and pulling the area open in shear fashion. Wearers of disposable absorbent pants are typically more mobile than diaper wearers, thus disposable absorbent pants may be more prone to getting snagged or caught on furniture or other protrusions in the environment. If such a snag or hang-up occurs, the disposable absorbent pant of the invention is designed to open at the seam so the pant can be refastened instead of being irreparably damaged thereby necessitating replacement of the damaged pant with a new pant.

In particular embodiments for improved fit and appearance of the disposable absorbent pant 20 of the present invention, at least one of the side panels 34 and 134 on each of the wearer's sides (left and right) desirably has a minimum length dimension that is about 10 percent or greater, and particularly about 25 percent or greater, of the overall length dimension of the disposable absorbent pant, measured parallel to the longitudinal axis 48. As used herein, the term "minimum length dimension" refers to the shortest distance between the waist opening and the leg opening on a side panel 34, 134, measured parallel to the longitudinal axis 48 of the garment. For example, in disposable absorbent pants having an overall length dimension of about 54 centimeters, the side panels 34 and 134 desirably have a minimum length dimension of about 6 centimeters or greater, such as about 14 centimeters. While each of the side panels 34 and 134 extend from the waist opening 50 to one of the leg openings 52, the front side panels 34 and/or back side panels 134 may have a continually decreasing length dimension moving from the chassis seam 72 to a distal edge 74 of the respective side panel 34, 134, as is best shown in the back side panels 134 in FIGS. 2 and 3.

The outer cover 40 suitably covers the front region 22, crotch region 26, and back region 24. In certain embodiments, part of the outer cover 40 may also cover, or form, the side panels 34, 134 as well, creating an all-encompassing, one-piece garment exterior. The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable body side liner 42 is made. While it is not a necessity for the outer layer to be liquid permeable, it is desired that it provides a relatively cloth-like texture to the wearer.

Necked-bonded laminates are particularly suitable for forming the outer cover 40. Necked-bonded laminates, in general, include at least one layer of necked or neckable material bonded to a stretchable or elastomeric layer. Necked-bonded laminates, and methods of making necked-bonded laminates, are taught, for example, in U.S. Pat. No. 5,910,224 to Morman, incorporated herein by reference.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Pliant Corporation of Schaumburg, Ill., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable breathable material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Certain non-breathable elastic films can also be used to make the outer cover 40. Examples of suitable non-breathable films can be made of styrene-ethylene-butylene-styrene or styrene-isoprene-styrene block copolymers, KRATON polymers from Kraton Polymers USLLC of Belpre, Ohio, U.S.A., metallocene catalyzed elastomers or plastomers, and the like. Other materials suitable for making the outer cover 40 include monolithic breathable films, such as those made of polyether amide based polymers, for example PEBAX, and ether/ester polyurethane thermal-plastic elastomers.

The liquid permeable body side liner 42 is illustrated as overlying the outer cover 40 and absorbent assembly 44, and may but need not have the same dimensions as the outer cover 40. The body side liner 42 is desirably compliant, soft feeling, and non-irritating to the wearer's skin. Further, the body side liner 42 can be less hydrophilic than the absorbent assembly 44, to present a relatively dry surface to the wearer and permit liquid to readily penetrate through its thickness.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner can be composed of a meltblown or spunbonded web of polyolefin fibers. The body side liner can also be a bonded-carded web composed of natural and/or synthetic fibers. The body side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL™ N-62 available from available from Uniqema Inc., a division of ICI of New Castle, Del., U.S.A. and GLUCOPON™ 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire body side liner 42 or can be selectively applied to particular sections of the body side liner, such as the medial section along the longitudinal centerline.

A suitable liquid permeable body side liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and body side liner 42 can include elastomeric materials, it can be desirable in some embodiments for the composite structure to be generally inelastic, where the outer cover, the body side liner and the absorbent assembly include materials that are generally not elastomeric.

The absorbent assembly 44 can be any structure which is generally compressible, conformable, non-irritating to the wearer's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The absorbent assembly 44 can have variable thickness, with greater thickness in target areas, such as in a central portion of the crotch region. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 can include an extremely thin absorbent composite material sold under the trade name NOVATHIN™ available from Rayonier Corporation located in Jessup, Ga., U.S.A., and/or an ultra-thin-absorbent (UTA) material including a mixture of SAP and pulp fiber. An example of a suitable UTA may include 3.7 grams (g) of FAVOR™ SXM 9543 SAP, available from Stockhausen GmbH & Co. KG located in Krefeld, Fed. Rep. of Germany, and 3.7 g of NB416 pulp fiber available from Weyerhauser located in Federal Way.

The chassis 32 can also incorporate other materials that are designed primarily to receive, temporarily store, and/or transport liquid along the mutually facing surface with the absorbent assembly 44, thereby maximizing the overall absorbent capacity of the absorbent assembly 44, if desired. One suitable material is referred to as a surge layer.

To enhance containment and/or absorption of body exudates, the disposable absorbent pant 20 may include a front waist elastic member 54, a rear waist elastic member 56, and leg elastic members 58, as are known to those skilled in the art (FIG. 3). Alternatively, instead of separate, disconnected front and rear waist elastic members 54, 56, an all-encompassing waist elastic member (not shown) that fully encircles the waist opening 50 of the disposable absorbent pant 20 may be included in the pant. The waist elastic members 54, 56 can be operatively joined to the outer cover 40 and/or body side liner 42 along the opposite waist edges 38 and 39, and can extend over part or all of the waist edges. The leg elastic members 58 are desirably operatively joined to the outer cover 40 and/or body side liner 42 along opposite side edges of the chassis 32 and positioned in the crotch region 26 of the disposable absorbent pant 20.

The waist elastic members 54, 56 and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA™ and available from E.I. DuPont de Nemours and Company, Wilmington, Del., U.S.A.

To further enhance containment and/or absorption of any body exudates discharged from the wearer, the chassis 32 may include a pair of containment flaps 46 which are configured to provide a barrier to the transverse flow of body exudates. A flap elastic member 53 (FIG. 3) may be operatively joined with each containment flap 46 in any suitable manner as is well known in the art. The elasticized containment flaps 46 define an unattached edge 60 which assumes an upright, generally perpendicular configuration in at least the crotch region 26 of the disposable absorbent pant 20 to form a seal against the wearer's body. The containment flaps 46 can be located along the leg openings, encircling at least a portion of each of the leg openings. Suitable constructions and arrangements for the containment flaps 46 are generally well known to those skilled in the art.

As described herein, the various components of the disposable absorbent pant can be assembled together employing various types of suitable attachment means, such as adhesive, sonic and thermal bonds or combinations thereof. The resulting product is a disposable absorbent pant with refastenable seams that have sufficient shear separation strength to remain fastened under normal use, but become unfastened under excessive shear force to avoid irreparable damage to the disposable absorbent pant.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

Tensile Test Method

This test measures the shear separation strength of a refastenable seam, the bonding strength of two bonded elements, the shear delamination strength of a laminate, and/or the shear separation strength or tear strength of a material. The force of separation is measured by determining load values as a specimen is pulled apart. For refastenable seams, laminates, and bonded elements, the force is applied parallel to the plane of contact of the joined materials, as illustrated by the test regions 102, 104, 106, 108, 110 in FIG. 4. The test values are an indication of how well the refastenable fastening system stays engaged against in-plane shear force, in relation to the strength of the underlying material(s) and of adjoining portions of a product, such as bonded areas, when subjected to similar force. The sample is pulled in a tensile tester until the sample pulls apart (or falls to 50% or less of peak load). Shear strength or tensile strength is the peak load result.

1. Overview

A rectangular material specimen is obtained by removing a segment of a training pant or other pant-type garment measuring about 1 inch (25.4 mm) by 6 inches (152 mm). The long dimension should be oriented substantially in the circumferential direction of the garment (FIG. 4). Each specimen may comprise a fastening system, a bonded region, and/or raw material(s). Suitable fastening systems include hook and loop fastening systems, as well as adhesive, cohesive, self-engaging and other types of refastenable fastening systems, suitably incorporated into a disposable absorbent pant as described herein. If a specimen includes a portion of an absorbent core of the garment that is unattached to the material layer(s) of interest, the absorbent may be removed prior to the test. In addition, any seams or bond areas should be located substantially in the middle of the long direction of each specimen (see regions 104, 106, 108, 110 in FIG. 4), and should run from one long edge to the other. Alternatively, a portion of a disposable absorbent garment that does not include a fastening system may be tested. Care should be taken with any material sample to ensure that the long dimension of each specimen of the sample corresponds to the circumferential direction of the garment. Finally, if a refastenable seam possesses greater shear strength at leg and/or waist edges than in a middle portion of the seam, the seam may be sampled at both high and low strength zones (see FIG. 4).

The specimen is placed between clamps on a tensile tester. One narrow end of the specimen is held in the upper clamp, while the other is held in the lower clamp; the long dimension of the specimen is the direction of tensile testing. The fastening system or bond, if present, is arrayed between the clamps, approximately parallel to the edges of the clamp faces and approximately evenly spaced between them. The gage length is 2 inches (50.8 mm) between the edges of the clamp faces. The term "load" refers to the gram value measured by the load cells in the tensile tester.

The jaws are separated at a controlled rate until the specimen breaks (falls to 50% or less of peak load), or until the two bonded or fastened components come apart. The load values generated on the material throughout this process are recorded.

In the case where a sample comprises more than one variable, such as a refastenable seam formed from discrete layers of material joined by a refastenable fastener, the fastener of which is bonded to one of the layers, several possible independent failure modes are contemplated. For example, the refastenable seam may separate in a shear mode, the fastener may tear off the underlying material to which it was bonded, or the underlying material may tear or delaminate. The peak load at sample rupture is assigned to the system that fails first, i.e., the system that causes the rupture. The remaining system(s) in the sample specimen may be inferred to possess greater strength under tensile strain than the measured peak load value for the specimen.

Data from specimens of non-standard widths should be normalized to a 1-inch (25.4-mm) effective specimen width by multiplying or dividing by the factor by which the specimen width deviates from 1 inch (25.4 mm). For example, the peak load value derived by pulling apart a 3-inch (76.2 mm) wide specimen should be divided by 3. Normalized 1-inch specimen peak load values are used for calculation of averages and strength ratios.

At least four specimens of each sample should be tested, and the results averaged. If specimens of a single sample differ in failure modes (i.e., one specimen exhibits shearing of the fastened region, while another exhibits delamination of underlying material), an attempt should be made by additional testing to obtain data for four specimens exhibiting the most frequent failure type(s) observed. Results of the first four specimens exhibiting the same failure mode should be averaged.

2. Apparatus and Materials 2.1 Constant Rate of Extension (CRE) tensile tester such as an MTS tensile tester model Synergie 200 Test Bed, available from MTS Systems Corporation, Research Triangle Park, N.C., U.S.A.

2.2 Load cells: A suitable cell selected so the majority of the peak load values fall between 10 and 90% of the manufacturer's recommended ranges of load cell's full scale value; for example, Model 100N available from MTS Systems Corporation, Research Triangle Park, N.C., U.S.A.

2.3 Operating software and data acquisition system such as MTS TestWorks® for Windows® software version 4, available from MTS Systems Corporation, Research Triangle Park, N.C., U.S.A.

2.4 Grips: pneumatic-action grips, top and bottom, identified as part number 38.00716 available from MTS Systems Corporation.

2.5 Grip faces: 25 by 75-mm (1 by 3-inch) interlocking faces such as are available from MTS Systems Corporation.

3. Conditioning

Reasonable ambient conditions should be used for sample testing, such as 73±2 degrees Fahrenheit and a relative humidity of 50±2%. The instruments used should be calibrated as described in the manufacturer's instructions for each instrument.

4. Procedure

Tensile Tester test conditions:

| | |
|---|---|
| Break sensitivity | 50% |
| Break threshold | 3 grams force/millimeter sample width |
| Preload? | No |
| Test speed | 508 ± 10 mm/min |
| Gage length | 2 inches (50.8 mm) |
| Number of cycles | 1 |

A. Using the tensile frame pushbutton controls for crosshead position, move grips to provide a gage length of 2 inches (50.8 mm). Tare the crosshead channel to this initial gage length.

B. Without touching the fastening area, place a material specimen so that the fastener or bonded seam (if present) is centered (vertically) between the grips, held in a centered position (horizontally) within each grip, and oriented correctly (1 inch/25.4 mm dimension running the width direction on the grips).

C. Close the upper grips on the specimen and tare the load channel.

D. Hold the specimen in such a way as to minimize slack in the specimen, but do not place the specimen under tension, and close the lower grips on the specimen.

E. Run the test using the above parameters by clicking on the RUN button. If specimens are observed to slip when held in grip faces, the surfaces of the grips should be adapted to provide a higher friction surface. Data from specimens on which slippage occurred should be discarded.

F. When the test is complete, save the data to a sample file.

G. Remove the specimen from the grips.

H. Run additional specimens of a given sample using steps B-E and G; the data for all specimens should be saved to a single file.

I. Continue testing all samples in this manner.

J. Data are reported as the average peak load value for each sample.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A disposable absorbent pant comprising: a chassis including a front region and a back region, and defining a waist opening and first and second leg openings; a first refastenable seam extending from the wrist opening to the first leg opening between the front region and the back region; and a second refastenable seam extending from the waist opening to the second leg opening between the front region and the back region; wherein each of the first and second refastenable seams has a shear separation strength that is greater along a waist-end portion and along a leg-end portion of each seam compared to a mid-portion of each seam and wherein the shear separation strength of each of the first and second refastenable seams is between about 0.7 and about 1.2 kilograms on a 1-inch wide sample; the shear separation strength of each of the first and second refastenable seams is less than a tensile strength of the front and back regions, and the shear separation strength of each of the first and second refastenable seams is less than a delamination strength of two laminated layers in the front and/or back regions, the laminated layers including at least two of the group consisting of a nonwoven, a film, and an adhesively-bonded elastomeric nonwoven composite.

2. A disposable absorbent pant, comprising: a chassis including a front region and a back region, and defining a waist opening and first and second leg openings; a first refastenable seam extending from the waist opening to the first leg opening between the front region and the back region and including a first fastening component bonded to one of the front region and the back region; and a second refastenable seam extending from the waist opening to the second leg opening between the front region and the back region and including a second fastening component bonded to one of the front region and the back region; wherein each of the first and second refastenable seams has a greater shear separation strength along a waist-end portion and along a leg-end portion of each seam compared to a mid-portion of each seam; wherein a bonding strength between the first fastening component and the region to which the first fastening component is bonded is greater than a shear separation strength of the first refastenable seam; and wherein a bonding strength between the second fastening component and the region to which the second fastening component is bonded is greater than a shear separation strength of the second refastenable seam.

3. The disposable absorbent pant of claim 1, having a ratio of shear separation strength of one of the first and second refastenable seams to tensile strength of the front and back regions between about 0.01 and about 0.99 per unit of seam length.

4. The disposable absorbent pant of claim 1, having a ratio of shear separation strength of one of the first and second refastenable seams to tensile strength of the front and back regions between about 0.1 and about 0.9 per unit of seam length.

5. The disposable absorbent pant of claim 1, having a ratio of shear separation strength of one of the first and second refastenable seams to tensile strength of the front and back regions between about 0.3 and about 0.8 per unit of seam length.

6. The disposable absorbent pant of claim 1, wherein each of the first and second refastenable seams has a shear separation strength less than a tensile strength of an outer cover comprising the front and back regions.

7. The disposable absorbent pant of claim 6, wherein the outer cover has a delamination strength greater than the shear separation strength of the first refastenable seam.

8. The disposable absorbent pant of claim 6, wherein the outer cover comprises a stretchable material.

9. The disposable absorbent pant of claim 1, wherein each of the first and second refastenable seams has a shear separation strength less than a tensile strength of a body side liner comprising the front and back regions.

10. The disposable absorbent pant of claim 9, wherein the body side liner has a delamination strength greater than the shear separation strength of the first refastenable seam.

11. The disposable absorbent pant of claim 1, wherein the front region comprises two front side panels bonded to a front center panel along first and second front chassis seams and the back region comprises two back side panels bonded to a back center panel along first and second back chassis seams, and each of the first and second refastenable seams has a shear separation strength less than a tensile strength of any of the front and back side panels.

12. The disposable absorbent pant of claim 11, wherein each of the front chassis seams and the back chassis seams has a bonding strength greater than the shear separation strength of each of the refastenable seams.

13. The disposable absorbent pant of claim 11, wherein each of the front and back side panels has a delamination strength greater than the shear separation strength of the first refastenable seam.

14. The disposable absorbent pant of claim 11, wherein each of the front side panels comprises a stretchable material.

15. The disposable absorbent pant of claim 11, wherein each of the back side panels comprises a stretchable material.

16. The disposable absorbent pant of claim 1, wherein the first refastenable seam comprises a first fastening component bonded to the chassis with a bonding strength between the first fastening component and the chassis being greater than the shear separation strength of the first refastenable seam, and the second refastenable seam comprises a second fastening component bonded to the chassis with a bonding strength between the second fastening component and the chassis being greater than the shear separation strength of the second refastenable seam.

17. The disposable absorbent pant of claim 2, having a ratio of shear separation strength of the first refastenable seam to bonding strength between the first fastening component and the panel to which the first fastening component is bonded, between about 0.01 and about 0.99 per unit of seam length.

18. The disposable absorbent pant of claim 2, having a ratio of shear separation strength of the first refastenable seam to bonding strength between the first fastening component and the panel to which the first fastening component is bonded, between about 0.1 and about 0.9 per unit of seam length.

19. The disposable absorbent pant of claim 2, having a ratio of shear separation strength of the first refastenable seam to bonding strength between the first fastening component and the panel to which the first fastening component is bonded, between about 0.3 and about 0.8 per unit of seam length.

20. The disposable absorbent pant of claim 2, wherein the shear separation strength of each of the first and second refastenable seams is between about 0.3 and about 2.7 kilograms on a 1-inch wide sample.

21. The disposable absorbent pant of claim 2, wherein the shear separation strength of each of the first and second refastenable seams is between about 0.5 and about 1.7 kilograms on a 1-inch wide sample.

22. The disposable absorbent pant of claim 2, wherein the shear separation strength of each of the first and second refastenable seams is between about 0.7 and about 1.2 kilograms on a 1-inch wide sample.

23. The disposable absorbent pant of claim 2, wherein the front region comprises a stretchable material.

24. The disposable absorbent pant of claim 2, wherein the back region comprises a stretchable material.

25. The disposable absorbent pant of claim 2, wherein the front region comprises a first front side panel and a second front side panel attached to opposite edges of a front center panel.

26. The disposable absorbent pant of claim 2, wherein the back region comprises a first back side panel and a second back side panel attached to opposite edges of a back center panel.

* * * * *

UNITED STATES PATENT AND TRADEMARK OFFICE
CERTIFICATE OF CORRECTION

PATENT NO. : 7,637,898 B2  Page 1 of 1
APPLICATION NO. : 10/222216
DATED : December 29, 2009
INVENTOR(S) : Kuen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1605 days.

Signed and Sealed this

Twenty-first Day of December, 2010

David J. Kappos
*Director of the United States Patent and Trademark Office*